United States Patent
Salunke et al.

(10) Patent No.: US 7,235,678 B2
(45) Date of Patent: Jun. 26, 2007

(54) BILE ACID DERIVED STEROIDAL DIMERS WITH NOVEL AMPHIPHILIC TOPOLOGY HAVING ANTIFUNGAL ACTIVITY

(75) Inventors: Deepak Bhalchandra Salunke, Maharashtra (IN); Braja Gopal Hazra, Maharashtra (IN); Vandana Sudhir Pore, Maharashtra (IN); Mukund Vinayak Deshpande, Maharashtra (IN); Pallavi Balaram Nahar, Maharashtra (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/815,109

(22) Filed: Mar. 30, 2004

(65) Prior Publication Data

US 2005/0222115 A1    Oct. 6, 2005

(51) Int. Cl.
*C07J 9/00* (2006.01)

(52) U.S. Cl. .................................... 552/509

(58) Field of Classification Search ................ 514/182; 552/509
See application file for complete search history.

(56) References Cited

U.S. PATENT DOCUMENTS 5,250,524 A * 10/1993 Kramer et al. .............. 514/177

OTHER PUBLICATIONS

Pandey et al., "Synthesis of a Head to Head Cholaphane", Tetrahedron Letters, vol. 38(28), pp. 5045-5046, 1997.*
Salunke et al., "New Steroidal Dimers with Antifugal and Antiproliferative Activity", J. Med. Chem., vol. 47, pp. 1591-1594, 2004.*

* cited by examiner

*Primary Examiner*—Barbara P. Badio
(74) *Attorney, Agent, or Firm*—Ladas & Parry LLP

(57) ABSTRACT

The need for new class of antifungal drugs with high efficacy, low toxicity and novel mode of action is well established. Synthesis and antifungal activity of bile acid derived new steroidal dimers $N^1,N^3$-Diethylenetriamine bis [cholic acid amide] (1) and $N^1,N^3$-Diethylenetriamine bis [deoxycholic acid amide] (2) having novel amphiphile topology is described.

3 Claims, 1 Drawing Sheet

BILE ACID DERIVED STEROIDAL DIMERS WITH NOVEL AMPHIPHILIC TOPOLOGY HAVING ANTIFUNGAL ACTIVITY

FIELD OF INVENTION

The following specification particularly describes and ascertains the nature of this invention and the manner in which it is to be performed:

This invention relates to new compounds $N^1,N^3$-diethylenetriamine bis[cholic acid amide] of formula (1), $N^1,N^3$-diethylenetriamine bis[deoxycholic acid amide] of formula (2)

for the treatment of fungal infections include amphotericin B and a variety of azoles. Amphotericin B is reported to be toxic to humans and clinical resistance to azoles is increasing. Therefore there is need to screen for new drugs with high efficacy, low toxicity and to which microbes are unlikely to develop resistance.

Since the compounds having structural formula (1) and (2) have not been reported in the literature, there is no known process at present for their synthesis. The inventors are reporting a new process for the synthesis of these novel dimeric steroids having structural formulae (1) and (2) for the first time.

Formula (1)

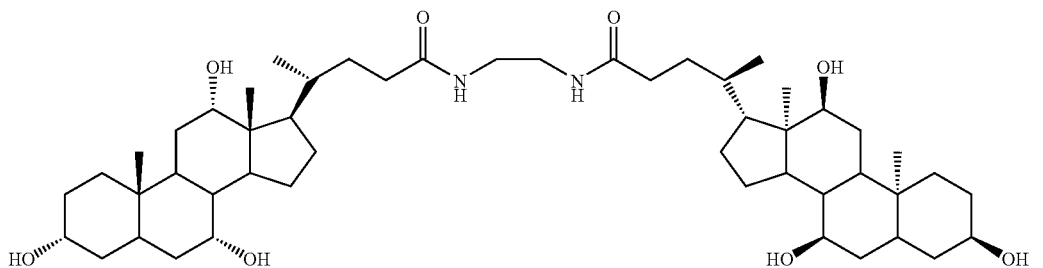

Formula (2)

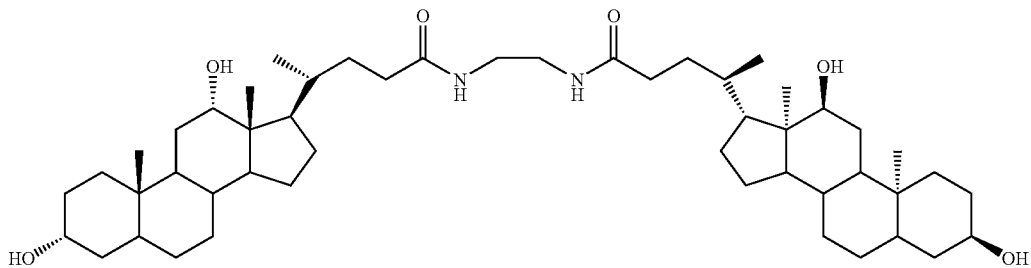

having novel amphiphilic topology as shown in FIG. 1 with anti fungal activity and process for the preparation thereof from N-succinimidyl ester of cholic acid and deoxycholic acid having structural formulae (4) and (5) respectively.

Formula (4)

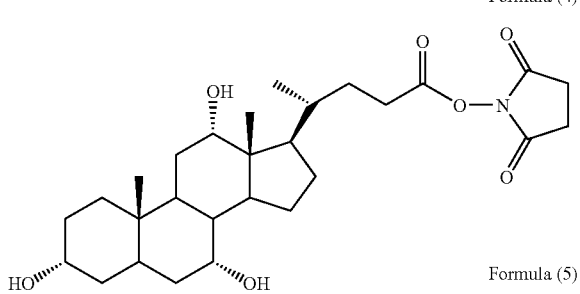

Formula (5)

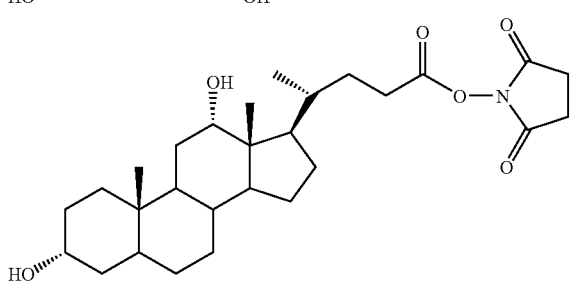

During the last four decades, there has been tremendous increase in the frequency of fungal infections. Current drugs The title compounds having structural formulae (1) and (2) are found to possess novel amphiphilic topology and show very good antifungal activity and the results have been incorporated in this specification.

Compound having structural formula (4) and (5) can be prepared from cholic acid or deoxycholic acid and N-hydroxy succinimide in the presence of dicyclohexylcarbodiimide. [Reference: Okahata, Y.; Ando, R.; Kunitake, T. *Bull. Soc. Chem. Jpn.* 1979, 52, 3647-3653]

BACKGROUND AND PRIOR ART REFERENCES

Steroidal dimers have tremendous applications in different areas such as molecular architecture and engineering, physical-organic chemistry, pharmacology and catalysis. [Reference: Yuexian Li; Dias, R. *Chem. Rev.* 1997, 97, 283-304 and Davis, A. P. *Chem. Soc. Rev.* 1993, 243-253]. Eur. Pat. Application EP 489423 describes a process for the preparation of bile acid derivatives and their use in medicine. In this patent application different types of steroidal dimers have been synthesized as inhibitors of bile acid resorption than the compounds described in the present invention. Compounds having structural formulae (1) and (2) have not been reported in the literature. Furthermore in the above mentioned reference amphiphilic topology of compounds (1) and (2) and their biological activity have not been mentioned. Compounds having structural formulae (1) and (2) show this novel amphiphilic topology as well as remarkable antifungal activity.

OBJECTS OF THE INVENTION

Main objective of this invention is to provide the steroidal dimers having structural formulae (1) and (2) showing novel amphiphilic topology and a process for the preparation thereof.

Another object is to provide the antifungal activity of the said steroidal dimers.

DETAILED DESCRIPTION OF THE INVENTION

Figure 1:
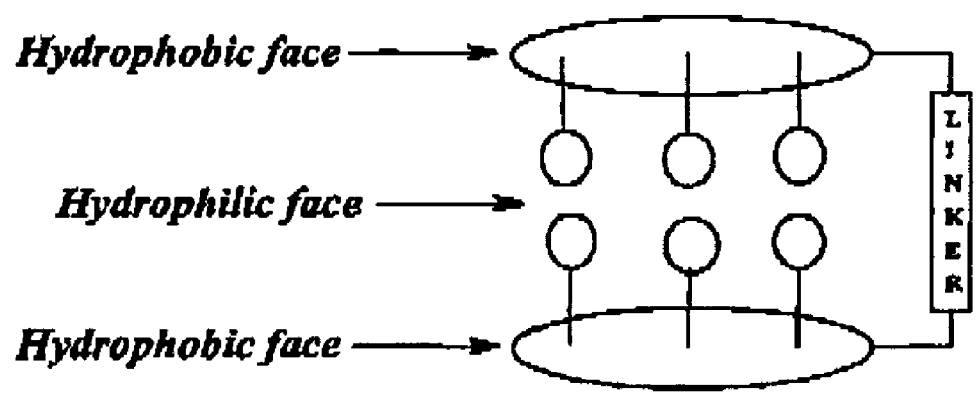
FIG. 1 shows an example of the amphiphilic topology of the steroidal dimers having a partially rigid structure with three discrete faces, wherein one polar face is sandwiched within two non-polar faces.

Accordingly the present invention provides steroidal dimers having structural formula (1)

partially rigid structure with three discrete faces, one polar face sandwiched within two non-polar faces.

In an embodiment of the invention the bile acid used in step 1 may be cholic acid or deoxycholic acid.

In yet another embodiment Antifungal steroidal dimers as claimed in claim 1, wherein the said compounds show antifungal activity against both pathogenic and non-pathogenic fungi.

In an embodiment the pathogenic fungi is *C. albicans*.

In a further embodiment wherein the non-pathogenic fungi are *B.poitrassi* and *Y. lipolytica*.

In yet another embodiment the minimum inhibitory concentration (MIC) of compound of formula I is about 11.30 nm and MIC of compound of formula 2 is in the range of 11.75 nm to 23.50 nm.

In an embodiment A process for the preparation of steroidal dimers $N^1,N^3$-diethylenetriamine bis and $N^1,N^3$-di-

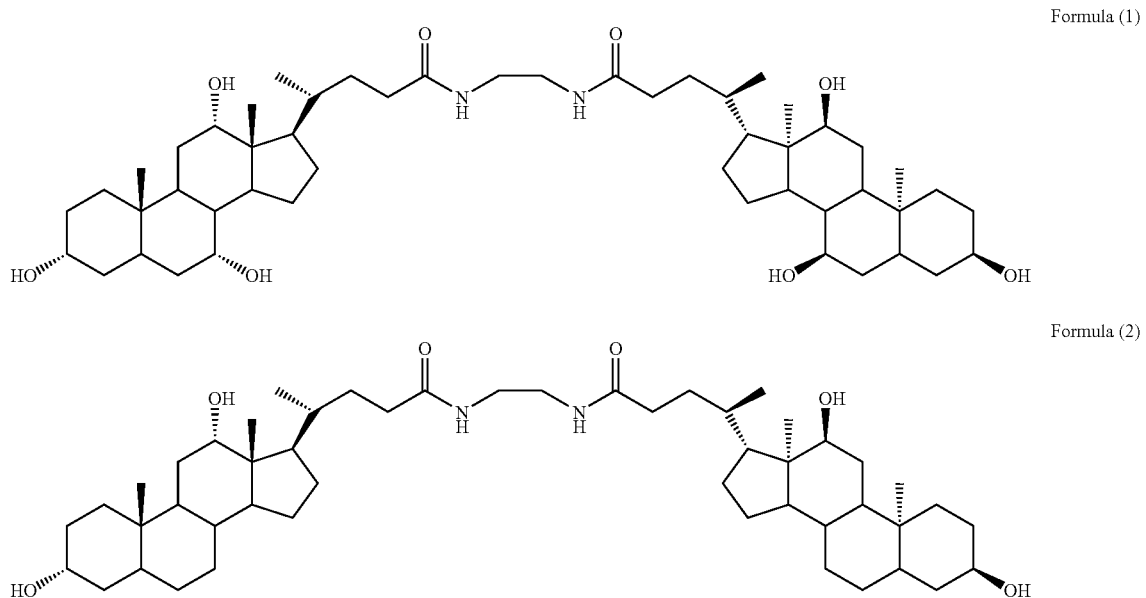

Formula (1)

Formula (2)

In yet another embodiment wherein the Antifungal steroidal dimmers have amphiphilic topology as shown in FIG. 1 and ethylenetriamine bis having structural formula (1) and (2) respectively,

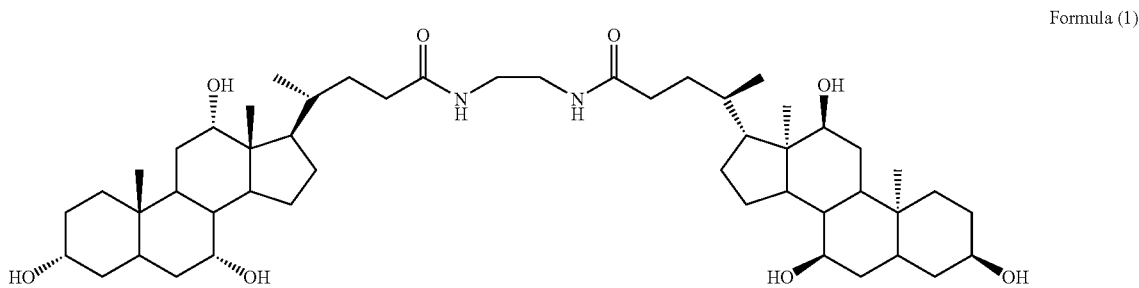

Formula (1)

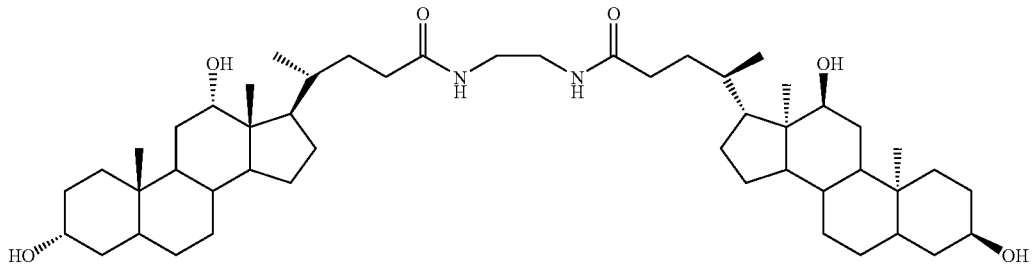

Formula (2)

a. preparing a solution of N-succinimidyl ester of bile acids in an organic solvent at a temperature ranging between 10 to 50° C.;
b. adding diethylenetriamine to the solution of step (a) followed by stirring the same for a time duration ranging from 1 to 5 h at a temperature ranging between 20 to 70° C. to obtain a reaction mixture;
c. quenching the reaction mixture of step (b) with ice to a form containing crude products having structural formula (a) and (b), and
d. separating the crude products of step (c) and purifying the same to obtain (1) or (2).

In another embodiment the organic solvents used in step 1 for the preparation of N-succinimidyl ester solutions may be chlorinated solvents such as chloroform and dichloromethane or polar aprotic solvents such as dimethylformamide and dimethylsulfoxide.

In the feature of present invention the crude products (1) and (2) may be purified by column chromatography using silica gel, basic alumina, neutral alumina as adsorbants and ethylacetate-hexane, ethylacetate, ethylacetate-chloroform, chloroform-methanol as solvent systems.

The compounds (1) and (2) of the present invention represents novel amphiphilic topology that has not previously described, having partially rigid structure with three discrete faces, one polar face sandwiched within two non polar faces as shown in FIG. (3) drawn in this specification. Compound (1) of the present invention shows very good antifungal activity for *Candida albicans* (five isolates), *Benjaminiella poitrasii* and *Yarrowia lipolytica* as compaired with standard drug cycloheximide. The compound (2) has moderate antifungal activity. The results suggests that the compound (1) and (2) have potential as antifungal agents when compared to standard inhibitor cycloheximide, when tested against both pathogenic as well as non-pathogenic fungi.

The following examples illustrate several preferred embodiments to describe the invention however it should be construed to limit the scope of the present invention.

EXAMPLE 1

N-succinimidyl ester (4) (1.01 g, 2 mmol) of cholic acid was dissolved in 2 ml of dimethylformamide. To it diethylenetriamine (0.12 ml, 1.1 mmol) was added at 50° C. and reaction mixture was stirred for the period of 1 h at 70° C. Reaction was quenched by the addition of crushed ice. Solid crude product was filtered, washed with cold water and dried under vacuum. Column chromatographic purification of the crude product [Neutral deactivated alumina, eluent: chloroform/methanol (4:1)] afforded $N^1,N^3$-Diethylenetriaminebis [cholic acid amide] (1) (0.84 g, 95%). It was further recrystallized from methanol/chloroform. Mp=168° C. (colourless powder). IR (Nujol): 3298 bs, 2921 bs, 1650 bs cm$^{-1}$. $^1$H NMR (500 MHz, CD$_3$OD+CDCl$_3$): 3.95 [s, 2×H—C (12, 12')], 3.83 [bs, 2×H—C (7, 7')], 3.37 [m, 2×H—C (3, 3')], 3.32 [m, 4×H—C (25, 25')], 2.27 [m, 4×H—C (26, 26')], 1.01 [d, J=5 Hz, 2×CH$_3$—C (20, 20')], 0.90 [s, 2×CH$_3$—C (13, 13')], 0.69 [s, 2×CH$_3$—C (10, 10')]. $^{13}$C NMR (125 MHz, CD$_3$OD+CDCl$_3$): 175.42, 72.82, 71.38, 68.04, 48.03, 46.23, 46.15, 41.17, 41.30, 39.25, 39.07, 38.48, 35.22, 35.10, 34.52, 34.37, 32.54, 31.39, 29.76, 27.88, 27.29, 26.20, 22.95, 22.16, 16.95, 12.12. MS (LCMS, methanol, water, and ammonium acetate, m/z): 885.01 ([M+H]$^+$, 86), 495.03 (20), 416.04 (39), 407.04 (66), 398.04 (100), 389.04 (94), 279.05 (17), 225.05 (76). $[\alpha]_D^{25}$=+8.264 (c=0.605, methanol).

EXAMPLE 2

N-succinimidyl ester (5) (0.98 g, 2 mmol) of deoxycholic acid was dissolved in 2 ml of dimethylformamide. To it diethylenetriamine (0.073 ml, 1.1 mmol) was added at 30° C. and reaction mixture was stirred for the period of 2 h at 50° C. Reaction was quenched by the addition of crushed ice. Solid crude product was filtered, washed with cold water and dried under vacuum. Column chromatographic purification of the crude product [Neutral deactivated alumina, eluent: chloroform/methanol (5:1)] afforded $N^1,N^3$-Diethylenetriaminebis [deoxycholic acid amide] (2) (0.84 g, 98%). It was further recrystallized from methanol/chloroform. Mp=130° C. (colourless powder). IR (Nujol): 3298 bs, 2921 m, 1650 bs cm$^{-1}$. $^1$H NMR (500 MHz, CD$_3$OD+CDCl$_3$): 3.97 [s, 2×H—C (12, 12')], 3.57 [m, 2×H—C (3, 3')], 3.33 [m, 4×H—C (25, 25')], 2.70[m, H—C (26, 26')], 0.99 [d, J=5 Hz, 2×CH$_3$—C (20, 20')], 0.91 [s, 2×CH$_3$—C (13, 13')], 0.67 [s, 2×CH$_3$—C (10, 10')]. $^{13}$C NMR (125 MHz, CD$_3$OD+CDCl$_3$): 174.82, 72.97, 71.40, 48.43, 48.14, 46.60, 46.44, 42.04, 38.90, 38.78, 36.23, 35.97, 35.29, 34.10, 33.58, 32.92, 31.50, 30.20, 28.54, 27.50, 27.10, 26.17, 23.69, 23.10, 17.24, 12.57. MS (LCMS, methanol, water, and ammonium acetate, m/z): 853.05 ([M=H]$^+$, 50), 505.05 (24), 479.05 (100), 149.03 (12). $[\alpha]_D^{25}$=+39.228 (c=1.555, methanol).

EXAMPLE 3

This example illustrates the antifungal activity of the compounds of the present invention.

Pharmacological Evaluation

Antifungal Activity. Materials and Methods: *Candida albicans* (5 isolates), *Benjaminiella poitrasii* and *Yarrowia*

*lipolytica* maintained on Difco Yeast extract peptone glucose agar slants at 28° C. for 7 days. *C. albicans* and *Y. lipolytica* were inoculated in YPG broth at 28° C. and *B. poitrasii* at 37° C. for 24 hours. Compounds (1) and (2) were solubilized in DMSO and stock solution of 1 mg/ml was prepared. Cycloheximide, a standard inhibitor, was also dissolved in DMSO and varying concentrations were added on to the filter paper discs.

Antibiotic inhibition assay using disc method: 100 μL of the yeast cell suspensions for all five *C. albicans* isolates, *B. poitrasii* and *Y. lipolytica* were spread plated on sterile YPG agar plates separately. Five sterile whatman filter paper discs were placed on each plate. To the central disc, DMSO was added as the control and to other four discs, different concentrations of the compounds were added. The plates were then incubated at 28° C. for 24 hours and were observed for the zone of inhibition around the disc. The minimum concentration that gave the zone of inhibition was determined as the minimum inhibitory concentration (MIC) of the compound for that fungal culture. All the experiments were done in triplicates. Similar procedure was followed to determine the MIC of cycloheximide.

Antifungal Activity. Compounds (1) and (2) were examined for antifungal activity. The MIC for compound (1) is 11.32 nM for all five *C. albicans* isolates, *B. poitrassi* and *Y. lipolytica,* the MIC values for the compound (2) ranged between 10-25 nM. However, in case of cycloheximide, the MIC value is much higher and ranged between 250-500 nM for isolates of *C. albicans*. In a microtitre dilution broth assay, the MIC of cycloheximide against a clinical isolate of *C. albicans* was reported to be greater than 900 nM. MIC of cycloheximide was 71 nM in *B. poitrasii* and 106 nM in *Y. lipolytica*.

TABLE 1

In Vitro antifungal activities of compounds (1), (2) and cycloheximide.

| Fungi | Compound (1) | | Compound (2) | | Cycloheximide | |
|---|---|---|---|---|---|---|
| | MIC NM | Inhibition Zone, cm | MIC nM | Inhibition Zone, cm | MIC nM | Inhibition Zone, cm |
| *C. albicans*, Isolate no. 1 | 11.32 | 0.8 | 11.75 | 0.9 | 355.8 | 1.0 |
| *C. albicans*, Isolate no. 2 | 11.32 | 0.8 | 11.75 | 0.7 | 538.8 | 0.9 |
| *C. albicans*, Isolate no. 3 | 11.32 | 0.8 | 11.75 | 1.0 | 266.9 | 0.9 |
| *C. albicans*, Isolate no. 4 | 11.32 | 0.8 | 11.75 | 0.8 | 533.8 | 1.0 |
| *C. albicans*, Isolate no. 5 | 11.32 | 0.8 | 17.63 | 0.9 | 533.8 | 0.8 |
| *B. poitrassi* | 11.32 | 0.7 | 17.63 | 0.6 | 71.2 | 1.45 |
| *Y. lipolytica* | 11.32 | 0.9 | 23.50 | 0.8 | 106.8 | 0.9 |

The difference in the toxicity of cycloheximide towards *C. albicans,* a pathogenic fungus and *B. poitrasii* and *Y. lipolytica,* non-pathogenic fungi can be attributed to the differences in their cell wall composition that affects the passage of the compound through the fungal cell wall. DMSO did not show any zone of inhibition. The results suggest that the compounds (1) and (2) have potential as antifungal agents when compared to the standard inhibitor cycloheximide, when tested against both the pathogenic as well as non-pathogenic fungi.

We claim:

1. Antifungal steroidal dimers, $N^1,N^3$-diethylenetriamine bis [cholic acid amide] of formula (1), $N^1,N^3$-diethylenetriamine bis [deoxycholic acid amide] of formula (2)

Formula (1)

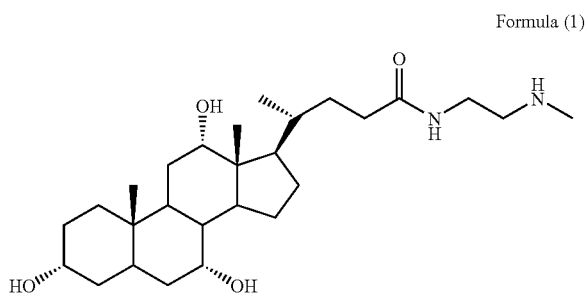

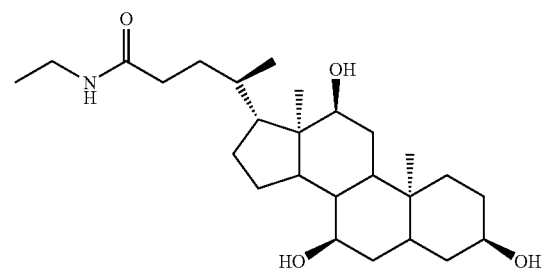

Formula (2)

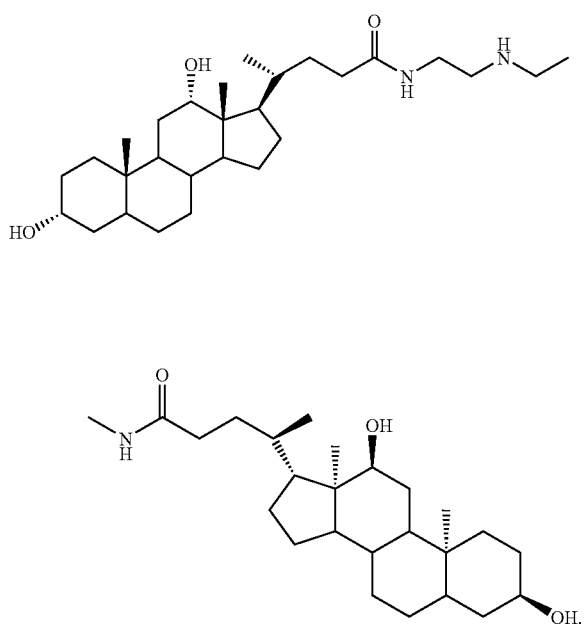

2. A method for the preparation of steroidal dimers $N^1,N^3$-diethylenetriamine bis [cholic acid amide] and $N^1,N^3$-diethylenetriamine bis [deoxycholic acid amide] having structural formula (1) and (2) respectively, Formula (1)

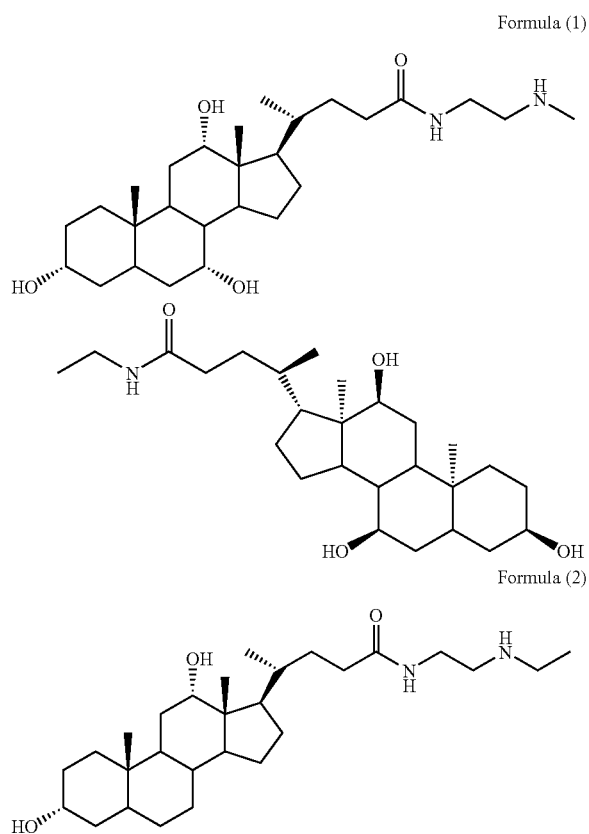

Formula (2)

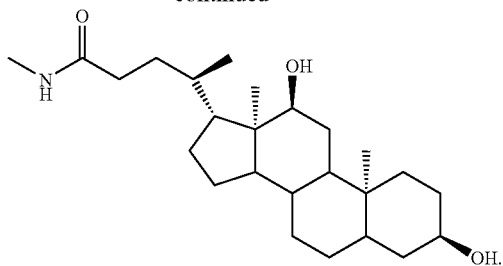

said method comprising,
- a. preparing a solution of N-succinimidyl ester of bile acids in an organic solvent at a temperature ranging between 10 to 50° C.;
- b. adding diethylenetriamine to the solution of step (a) followed by stirring the same for a time duration ranging from 1 to 5 h at a temperature ranging between 20 to 70° C. to obtain a reaction mixture;
- c. quenching the reaction mixture of step (b) with ice to a form containing crude products having structural formula (1) and (2), and
- d. separating the crude products of step (c) and purifying the same to obtain the compound of formula (1) or (2).

3. The method of claim 2, wherein the organic solvent is selected from a group comprising chlorinated solvents or polar aprotic solvents.

* * * * *